United States Patent [19]

Novotny et al.

[11] Patent Number: 5,533,512
[45] Date of Patent: Jul. 9, 1996

[54] METHOD AND APPARATUS FOR DETECTION OF VENOUS AIR EMBOLI

[75] Inventors: Mark A. Novotny, Westminster, Colo.; Thomas A. Boone, Laurel, Md.; Jeffrey D. Geisler, Salt Lake City, Utah; Garfield B. Russell, Mt. Gretna; John M. Graybeal, Grantville, both of Pa.

[73] Assignee: Ohmeda Inc., Liberty Corner, N.J.

[21] Appl. No.: 210,883

[22] Filed: Mar. 18, 1994

[51] Int. Cl.⁶ ........................................... A61B 5/08
[52] U.S. Cl. ............................ 128/719; 128/716
[58] Field of Search ........................ 128/716, 719

[56] References Cited

U.S. PATENT DOCUMENTS

| | | |
|---|---|---|
| Re. 34,153 | 12/1992 | Benner et al. . |
| 3,812,482 | 5/1974 | Clark . |
| 3,838,682 | 10/1974 | Clark et al. . |
| 3,910,256 | 10/1975 | Clark et al. . |
| 3,910,261 | 10/1975 | Ragsdale et al. . |
| 4,014,206 | 3/1977 | Taylor . |
| 4,109,505 | 8/1978 | Clark et al. . |
| 4,269,194 | 5/1981 | Rayburn et al. . |
| 4,280,495 | 7/1981 | Lampert . |
| 4,319,580 | 3/1982 | Colley et al. . |
| 4,371,786 | 2/1983 | Kramer . |
| 4,423,739 | 1/1984 | Passaro et al. . |
| 4,444,201 | 4/1984 | Itoh ................................. 128/716 |
| 4,543,328 | 9/1985 | Keller et al. . |
| 4,559,454 | 12/1985 | Kramer . |
| 4,671,295 | 6/1987 | Abrams et al. . |
| 4,676,639 | 6/1987 | Van Wagenen . |
| 4,722,347 | 2/1988 | Abrams et al. . |
| 4,784,486 | 11/1988 | Van Wagenen et al. . |
| 5,003,985 | 4/1991 | White et al. ................... 128/716 |
| 5,069,220 | 12/1991 | Casparie et al. .............. 128/719 X |
| 5,103,827 | 4/1992 | Smith . |
| 5,121,627 | 6/1992 | D'Aoust . |
| 5,135,304 | 8/1992 | Miles et al. . |
| 5,140,981 | 8/1992 | Lindstrom . |
| 5,197,481 | 3/1993 | Fisher . |
| 5,198,776 | 3/1993 | Carr . |
| 5,199,877 | 4/1993 | Page . |
| 5,231,591 | 7/1993 | Flewelling et al. . |
| 5,233,996 | 8/1993 | Coleman et al. . |
| 5,245,405 | 9/1993 | Mitchell et al. . |

OTHER PUBLICATIONS

Ohmeda Technical Report—*Real time nitrogen monitoring: a unique parameter in patient care.* © 1992 The BOC Group Inc.

Russell and Graybeal, *Raman Spectrometry for Detection of Venous and Arterial Air Embolism.* ASA Convention, Oct. 1993.

Matjasko, Petrozza and Mackenzie, *Sensitivity of End–tidal Nitrogen in Venous Air Embolism Detection in Dogs.* Anesthesiology 63:418–423, 1985.

Matjasko, Hellman and Mackenzie, *Venous Air Embolism, Hypotension, and End–tidal Nitrogen.* Neurosurgery 21:378–382, 1987.

(List continued on next page.)

*Primary Examiner*—Angela D. Sykes
*Assistant Examiner*—Stephen Huane
*Attorney, Agent, or Firm*—Roger M. Rathbun; Larry R. Cassett; Dennis H. Epperson

[57] ABSTRACT

Concomitant measurement of $EtCO_2$, $EtN_2$ and ($FiO_2$–$FeO_2$) concentrations are used to detect a VAE. In a respiratory gas monitoring system, continuous measurements of end-tidal carbon dioxide, end-tidal nitrogen and the difference between inspired and expired oxygen concentrations are averaged using a predetermined time period and stored as historical data. Periodically, a present value of each of these concentrations is compared to its respective historical average for a predetermined time period. If the following conditions are met, the device signals the presence of a venous air embolism: 1) a decrease in the $EtCO_2$ concentration of 1.5 mm Hg; 2) an increase in the $FeN_2$ concentration of 0.03 vol %; and 3) a decrease in the difference between the inspired oxygen concentration and the expired oxygen concentration of 0.20 vol %.

18 Claims, 4 Drawing Sheets

OTHER PUBLICATIONS

Mangan, Boucek, Powers and Shadduck, *Rapid Detection of Venous Air Embolism by Mass Spectrometry during Bone Marrow Harvesting*. Exp. Hematol. 13:639–640, 1985.

Russell, Richard and Snider, *Detection of Venous Air Embolism in Dogs by Emission Spectrometry*. J Clin Monit. 6:18–23, 1990.

Prager, Gregory, Ascher and Roberts, *Massive Venous Air Embolism during Orthotopic Liver Transplantation*. Anesthesiology 72:198–200, 1990.

Frankel and Holzman, *Air Embolism During Posterior Spinal Fusion*. Can J Anaesth 35:5:511–514, 1988.

Lew, Tay and Thomas, *Venous Air Embolism During Cesarean Section More Common Than Previously Thought*. Anesth Analg 77:448–452, 1993.

Drummond, Prutow and Scheller, *A Comparison of the Sensitivity of Pulmonary Artery Pressure, End–Tidal Carbon Dioxide, and End–Tidal Nitrogen in the Detection of Venous Air Embolism in the Dog*. Anesth Analg 64:688–692, 1985.

English, Westenskow, Hodges and Stanley, *Comparison of Venous Air Embolish Monitoring Methods in Supine Dogs*. Anesthesiology 48:425–429, 1978.

Losasso, Black, Muzzi, Michenfelder and Cucchiara, *Detection and Hemodynamic Consequences of Venous Air Embolism*. Anesthesiology 77:148–152, 1992.

Losasso, Muzzi, Dietz and Cucchiara, *Fifty Percent Nitrous Oxide Does Not Increase the Risk of Venous Air Embolism in Neurosurgical Patients Operated upon in the Sitting Position*. Anesthesiology 77:21–30, 1992.

Orebaugh, *Venous air embolism: Clinical and experimental considerations*. Critical Care Medicine, vol. 20, No. 8, pp. 1169–1177, Aug. 1992.

Russell and Graybeal, *Sensitivity of Venous Air Embolism Detection by Continuous Monitors of Oxygenation and Ventilation*. Anesthesiology V. 71, No. 3A, p. A133, Sep. 1989.

Bedford, *Perioperative Air Embolism*. Seminars in Anesthesia, vol. VI, No. 3, pp. 163–170, Sep. 1987.

Matjasko, Gunselman, Delaney and Mackenzie, *Sources of Nitrogen in the Anesthesia Circuit*. Anesthesiology 65:229, 1986.

Fong, Gadalla and Gimbel, *Precordial Doppler diagnosis of haemodynamically compromising air embolism during Caesarean section*. Can J Anaesth 1990/37:2/pp. 262–264.

Young, Smith, Murtagh, Vasquez and Levitt, *Comparison of Surgical and Anesthetic Complications in Neurosurgical Patients Experiencing Venous Air Embolism in the Sitting Position*. Neurosurgery vol. 18, No. 2, pp. 157–161, 1986.

Russell, Graybeal and Snider, *Rapid Pulmonary Excretion of Nitrogen Can Diagnose Arterial Air Embolism*. Anesthesiology V. 71, No. 3A, p. A137, Sep. 1989.

Russell, Snider, Richard, Rutherford and Loomis, *Recovery of Exhaled Nitrogen After Venous Air Embolism During Room Air Breathing as a Means to Assess Therapeutic Efficacy*. Anesthesiology v. 69, No. 3A, p. A552, Sep. 1988.

Mokriski, Nagle and Fragneto, *Does the Expired Carbon Dioxide Waveform Suggest Endobronchial Intubation?* J. Clin. Anesth., vol. 2., pp. 140–141, Mar./Apr. 1990.

Graybeal and Russell, *Relative Accuracy of Raman and Mass Spectrometry for Measuring End–Tidal Carbon Dioxide*. Anesthesiology V. 79, No. 3A, p. A562, Sep. 1993.

METHOD AND APPARATUS FOR DETECTION OF VENOUS AIR EMBOLI

FIELD OF THE INVENTION

This invention relates generally to the detection of venous air emboli and more specifically to an apparatus and method for the real time detection of venous air emboli which is based on the monitoring of a patient's inspired and expired respiratory gases.

BACKGROUND OF THE INVENTION

The occurrence of Venous Air Emboli (VAE) has been well documented in the medical literature. VAE has been shown to be a significant cause of mortality and morbidity in many different types of surgical procedures.

Venous Air Emboli occur when air bubbles enter the blood stream secondary to a negative pressure gradient. Negative pressure gradients can occur any time the surgical site is above the level of the right atrium. When air enters the venous system, small bubbles are formed. These bubbles travel to the right side of the heart, enter the right atrium, pass through the tricuspid valve into the right ventricle, through the pulmonic valve and into the pulmonary artery. As the bubbles traverse the pulmonary capillary tree, they become wedged in the distal pulmonary micro-vascular system. This results in increased pulmonary deadspace.

When gone undetected for sustained periods of time, it is possible for some bubbles to completely traverse the pulmonary capillary tree. These bubbles enter the left side of the heart and ultimately the arterial blood flow. Once inside the arterial circulation, the potential arises for severe intra-operative and/or post operative cardiopulmonary and neurological complications.

Precordial doppler has been shown to be a very specific and accurate detector of VAE. However, there are many problems associated with doppler monitoring. Positioning of the doppler probe over the correct intercostal space, electrosurgical interference, heart murmurs and the requirement of a trained ear make doppler monitoring less than adequate for VAE detection.

Continuous $CO_2$ monitoring is a sensitive indicator of VAE. However, $CO_2$ monitoring is very non-specific for VAE. There are many different physiological alterations that lower $CO_2$ values. Metabolic changes, cardiac output changes, hyperventilation and deadspace changes can lower expired $CO_2$ values.

Many studies have been performed to analyze conditions and parameters indicative of VAE. Several of these studies are summarized below.

Matjasko et al. (Matjasko, Petrozza and Mackenzie, *Sensitivity of End-tidal Nitrogen in Venous Air Embolism Detection in Dogs*. Anesthesiology 63:418–423, 1985) describes a study done to compare the sensitivity for the detection of venous air emboli of end-tidal nitrogen ($EtN_2$) monitoring, precordial Doppler (PD), end-tidal $CO_2$ ($EtCO_2$) and pulmonary artery pressure (PAP). This study concluded that: 1) precordial Doppler monitoring is the most sensitive qualitative detector of air entry into the superior vena cava and heart, however, it does not allow quantitative measurement of air entry into and dissipation from the lungs; and 2) changes in $EtN_2$ following low-dose infusion VAE are less sensitive than changes in $EtCO_2$, while during bolus VAE they are equally sensitive. Additionally, they expressed concern that shared operating room mass spectrometers would be sensitive enough and sample frequently enough to be of value in the early detection of clinical VAE.

Matjasko et al. (Matjasko, Hellman and Mackenzie, *Venous Air Embolism, Hypotension, and End-tidal Nitrogen*. Neurosurgery 21:378–382, 1987) describes a study done to compare the sensitivity for the detection of venous air emboli of end-tidal nitrogen ($EtN_2$) monitoring and end-tidal $CO_2$ ($EtCO_2$) monitoring during large bolus and infusion VAE.

Mangan et al. (Mangan, Boucek, Powers and Shadduck, *Rapid Detection of Venous Air Embolism by Mass Spectrometry during Bone Marrow Harvesting*. Exp. Hematol. 13:639–640, 1985) describes the detection of a venous air embolism by mass spectrometric monitoring of the patient's expired gases. They found that air emboli are suspected when end-tidal $CO_2$ decreases (down 1.5%) and also when expired nitrogen increases (up 4%).

Russell et al. (Russell, Richard and Snider, *Detection of Venous Air Embolism in Dogs by Emission Spectrometry*. J Clin Monit. 6:18–23, 1990) describes the detection of a venous air embolism by emission spectrometry monitoring of the end-tidal nitrogen and compares the results with monitoring by mass spectrometry.

Prager et al. (Prager, Gregory, Ascher and Roberts, *Massive Venous Air Embolism during Orthotopic Liver Transplantation*. Anesthesiology 72:198–200, 1990) reports the detection of a venous air embolism by mass spectrometric monitoring of the patient's end-tidal $CO_2$ and end-tidal expired nitrogen.

Frankel et al. (Frankel and Holzman, *Air Embolism During Posterior Spinal Fusion*. Can J Anaesth 35:5:511–514, 1988) presents a list of methods available for the detection of VAE including: precordial doppler, oesophageal stethoscope, measurements of end-tidal $CO_2$, end-tidal nitrogen, pulmonary artery pressure, transoesophageal echocardiography and transcutaneous $O_2$ and $CO_2$ monitoring.

Lew et al. (Lew, Tay and Thomas, *Venous Air Embolism During Cesarean Section More Common Than Previously Thought*. Anesth Analg 77:448–452, 1993) reports the use of a Raman scattering analyzer to continuously monitor inspired and expired nitrogen, oxygen, halothane, nitrous oxide, and end-tidal carbon dioxide levels via a side stream sampling catheter. Positive evidence of air embolism was defined as an increase in expired nitrogen concentrations of 0.1 vol % from the baseline.

Drummond et al. (Drummond, Prutow and Scheller, *A Comparison of the Sensitivity of Pulmonary Artery Pressure, End-Tidal Carbon Dioxide, and End-Tidal Nitrogen in the Detection of Venous Air Embolism in the Dog*. Anesth Analg 64:688–692, 1985) reports the results of an experiment seeking to define the relative sensitivities of end-tidal $CO_2$ analysis, end-tidal nitrogen analysis and pulmonary artery pressure (PAP) monitoring in the detection of VAE. They conclude that, where the capacity to identify increases in expired nitrogen on the order of 0.04% can be achieved, end-tidal nitrogen monitoring will identify VAE events with a sensitivity similar to that of PAP and $EtCO_2$. They also note that the difficulties inherent in achieving this level of nitrogen sensitivity represents a major limitation in the application of this test.

English et al. (English, Westenskow, Hodges and Stanley, *Comparison of Venous Air Embolism Monitoring Methods in Supine Dogs*. Anesthesiology 48:425–429, 1978) compares a variety of VAE monitoring methods for the detection of VAE including: precordial Doppler ultrasound frequency; end-tidal $CO_2$ concentration; mean pulmonary arterial, central venous and arterial pressures; esophageal heart sounds, including high-pitched barely audible tinkling sounds, enhanced second heart sound, systolic and mill-wheel murmurs; the electrocardiogram; arterial blood carbon dioxide and oxygen tensions; heart rate and the presence of cardiac arrhythmias.

None of these studies or the methods described therein disclose a monitoring system that automatically detects and signals the presence of a VAE. For example, the precordial Doppler techniques requires that a trained individual continuously monitor the output of the instrument and interpret the output. Likewise, while it is generally recognized that an increase in the end-tidal nitrogen concentration may be indicative of a VAE, or that a decrease in the end-tidal $CO_2$ concentration may be indicative of a VAE, neither is considered to be a reliable indicator. Additionally, as with the precordial Doppler, monitoring of end-tidal nitrogen and/or end-tidal $CO_2$ concentrations requires the attention of an operator to observe the behavior of these parameters and determine when changes therein are significant and whether they are indicative of a VAE or some other factor.

Thus, the ideal monitor for detection of venous air embolism should be: noninvasive; exquisitely sensitive; reliable; automatic; specific for air-induced changes; quantitatively reflect the size of the embolus; and have a duration of positive response accurately reflecting embolus onset and resolution. No single VAE monitor presently available meets all of these requirements.

SUMMARY OF THE INVENTION

The present invention is a venous air embolism detector which continuously monitors the respiratory gases of a patient and automatically signals the presence of a VAE. Continuous monitoring of the VAE detector of the present invention by an individual or subjective interpretations of its output are not required.

In one embodiment, the present invention measures and creates an historical average of the end-tidal $CO_2$ and end-tidal nitrogen concentrations for a predetermined period of time. At the end of that predetermined period of time, the current value of the end-tidal nitrogen concentration is compared to the previously acquired end-tidal nitrogen concentration historical average. If the current value exceeds the highest value of the historical average during the predetermined period of time by at least 0.03 vol %, a nitrogen "TRUE" value is set. Similarly, the current value of the end-tidal $CO_2$ concentration is compared to the previously acquired end-tidal $CO_2$ concentration historical average. If the current value is lower than the lowest value of the historical average during the predetermined period of time by at least 1.5 mmHg, a carbon dioxide "TRUE" value is set. When both the nitrogen and carbon dioxide values are "TRUE", the detector signals the presence of a VAE. Thus, the concomitant measurements of end-tidal $CO_2$ and end-tidal nitrogen concentrations are used to detect a VAE.

In another embodiment, an additional measurement based on the oxygen concentration is included in the test. During the same predetermined time period that the $CO_2$ and $N_2$ are being measured, the difference in the patient's inspired oxygen ($FiO_2$) and expired oxygen ($FeO_2$) concentrations are measured and averaged. If the current value of ($FiO_2$–$FeO_2$) is lower than the highest value of an historical average during the predetermined period of time by at least 0.02 vol %, an oxygen "TRUE" value is set. When the nitrogen, carbon dioxide and oxygen values are all "TRUE", the detector signals the presence of a VAE. Thus, the concomitant measurements of $EtCO_2$, $EtN_2$ and ($FiO_2$–$FeO_2$) concentrations are used to detect a VAE.

In a first embodiment, the present invention is an apparatus for detecting an air embolism comprising: a detector for detecting nitrogen in respiratory gases and determining the concentration of nitrogen in the respiratory gases; and a processor for analyzing the nitrogen concentration comprising: an historical data base of previously acquired nitrogen concentrations; a current data register which contains the current nitrogen concentration; and a comparator which compares the current nitrogen concentration with the historical data base and triggers an alarm signal if a predetermined comparison criteria is satisfied. The detector may be a Raman gas analyzer. Additionally, the processor may further comprise a peak detector which searches the historical data base of previously acquired nitrogen concentrations and determines the maximum value therein; and the comparator may further comprise a difference unit which determines the difference between the maximum historical nitrogen concentration and the value held in the current data register and signals an alarm if the difference exceeds a predetermined difference criteria. In some embodiments, the processor for analyzing the nitrogen concentration determines the end-tidal nitrogen concentration, $FeN_2$. In yet other embodiments, the comparator may further comprise an averager which determines an average derived from the data contained in the historical data base.

In a second embodiment, the invention is an apparatus for detecting an air embolism comprising: a detector for detecting carbon dioxide and nitrogen in respiratory gases and determining the concentrations of carbon dioxide and nitrogen in the respiratory gases; and a processor for comparing the carbon dioxide and nitrogen concentrations with a predetermined carbon dioxide concentration threshold and a predetermined nitrogen concentration threshold, respectively, the processor having an output which signals the presence of an air embolism when the carbon dioxide and nitrogen concentrations both cross the predetermined carbon dioxide concentration threshold and the predetermined nitrogen concentration threshold, respectively, within a predetermined time window. The detector may be a Raman gas analyzer. In some embodiments, the detector may further comprise means for detecting oxygen and the processor may further comprise a predetermined oxygen concentration threshold and signals the presence of an air embolism when the carbon dioxide, nitrogen and oxygen concentrations cross the predetermined carbon dioxide concentration threshold, the predetermined nitrogen concentration threshold and the predetermined oxygen concentration threshold, respectively, within a predetermined period of time.

In a third embodiment, the invention is for an apparatus for detecting an air embolism comprising: a detector for detecting nitrogen and carbon dioxide in respiratory gases; a gas analyzer for determining the breath-by-breath inspired and expired concentrations of the nitrogen and carbon dioxide in the respiratory gases; an end-tidal carbon dioxide analyzer which receives the measured breath-by-breath carbon dioxide concentrations and determines the value of the end-tidal carbon dioxide concentration, $EtCO_2$, therefrom for a plurality of breaths; an end-tidal carbon dioxide data memory for storing the plurality of breath-by-breath $EtCO_2$ values as a function of time; a nitrogen analyzer which receives the measured breath-by-breath nitrogen concentrations and determines the value of the expired nitrogen concentration, $FeN_2$, therefrom for a plurality of breaths; an expired nitrogen data memory for storing the plurality of breath-by-breath $FeN_2$ values as a function of time; and a processor which 1) compares the most recent value of $EtCO_2$ with previously acquired values of $EtCO_2$ and sets an $EtCO_2$ TRUE flag if a predetermined $EtCO_2$ comparison criteria is satisfied; 2) compares the corresponding most recent value of $FeN_2$ with previously acquired values of $FeN_2$ and sets an $FeN_2$ TRUE flag if a predetermined $FeN_2$ comparison criteria is satisfied; and 3) signals an alarm if the $EtCO_2$ TRUE flag and $FeN_2$ TRUE flag both occur for the same current breath. In some versions of this embodiment, the detector may further comprise an oxygen detector which detects oxygen in respiratory gases; the gas analyzer may further comprise an analyzer which determines the breath-by-breath inspired and expired concentrations of the oxygen in the respiratory gases; an oxygen analyzer which receives the measured breath-by-breath oxygen concentrations and determines the value of the inspired oxygen minus the expired oxygen concentration, $FiO_2-FeO_2$, therefrom for a plurality of breaths; an expired oxygen data memory for storing the plurality of breath-by-breath $FiO_2-FeO_2$ values as a function of time; and the processor may further comprise a processor which 4) compares the most recent value of $FiO_2-FeO_2$ with previously acquired values of $FiO_2-FeO_2$ and sets an $FiO_2-FeO_2$ TRUE flag if a predetermined $FiO_2-FeO_2$ comparison criteria is satisfied; and 5) signals an alarm if the $EtCO_2$ TRUE flag, the $FeN_2$ TRUE flag and the $FiO_2-FeO_2$ TRUE flag all occur for the same current breath. In some versions of this embodiment, the detector is a Raman gas analyzer. This embodiment may further comprise: a maximum value detector which extracts the highest value from the plurality of breath-by-breath $FeN_2$ values as a function of time which are stored in the expired nitrogen data memory; and a comparator which compares the most recent value of the expired nitrogen concentration $FeN_2$ with the maximum value and triggers an alarm when the most recent value exceeds the maximum value by at least 0.01 vol %. In other versions, this embodiment may further comprise: a minimum value detector which extracts the lowest value from the plurality of breath-by-breath $EtCO_2$ values as a function of time which are stored in the end-tidal carbon dioxide data memory; and a comparator which compares the most recent value of the end-tidal carbon dioxide concentration $EtCO_2$ with the lowest value and triggers an alarm when the most recent value is lower than the lowest value by at least 1.0 mmHg.

A fourth embodiment is for a method of automatically detecting an air embolism comprising the steps of: detecting nitrogen in respiratory gases; determining the breath-by-breath expired nitrogen concentration for a plurality of breaths and storing the plurality of breath-by-breath expired nitrogen concentrations in an historical data base; comparing the most recent value of the expired nitrogen concentration with previously acquired expired nitrogen concentrations in the historical data base; and signalling the presence of an air embolism when the most recent value of the expired nitrogen concentration crosses a baseline threshold derived from the previously acquired historical data base of expired nitrogen concentrations. This embodiment may further comprise the steps of: detecting carbon dioxide in respiratory gases; determining the breath-by-breath end-tidal carbon dioxide concentration for a plurality of breaths and storing the plurality of breath-by-breath end-tidal carbon dioxide concentrations in an historical data base; comparing the most recent value of the end-tidal carbon dioxide concentration with previously acquired end-tidal carbon dioxide concentrations in the historical data base; and signalling the presence of an air embolism when the most recent value of the end-tidal carbon dioxide concentration crosses a baseline threshold derived from the previously acquired historical data base of end-tidal carbon dioxide concentrations and the corresponding most recent value of the expired nitrogen concentration crosses a baseline threshold derived from the previously acquired historical data base of expired nitrogen concentrations. In another version, the step of signalling the presence of an air embolism further comprises the steps of: defining the nitrogen baseline threshold to be the highest expired nitrogen concentration in the nitrogen historical data base; and triggering the alarm when the most recent value of the expired nitrogen concentration exceeds the baseline threshold by at least 0.01 vol %. In yet another version of the method, the step of signalling the presence of an air embolism further comprises the steps of: defining the nitrogen baseline threshold to be the highest expired nitrogen concentration in the nitrogen historical data base; setting a nitrogen trigger when the most recent value of the expired nitrogen concentration exceeds the nitrogen baseline threshold by at least 0.01 vol %. In another version of the method, the step of signalling the presence of an air embolism further comprises the steps of: defining the end-tidal carbon dioxide baseline threshold to be the lowest end-tidal carbon dioxide concentration in the end-tidal carbon dioxide historical data base; setting an end-tidal carbon dioxide trigger when the most recent value of the end-tidal carbon dioxide concentration is lower than the end-tidal carbon dioxide baseline threshold by at least 1.0 mm Hg.

These and other characteristics of the present invention will become apparent through reference to the following detailed description of the preferred embodiments and accompanying drawings.

DETAILED DESCRIPTION OF THE PREFERRED EMBODIMENTS

Figure 1:
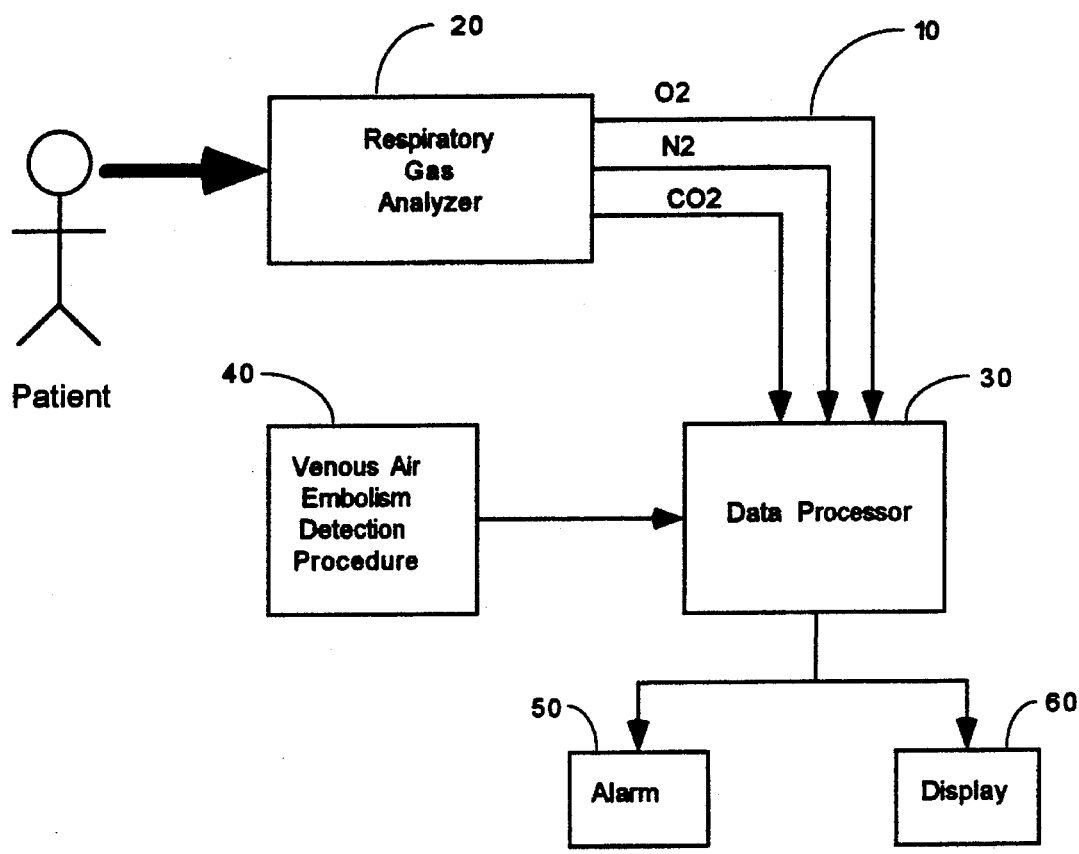
FIG. 1 shows a schematic diagram of the venous air embolism detector of the present invention.

FIG. 1 shows a schematic diagram of a venous air embolism detector 10 of the present invention. A respiratory gas analyzer 20 receives respiratory gases from a patient; analyzes the patient's respiratory gases; and sends signals corresponding to the concentrations of oxygen ($O_2$), nitrogen ($N_2$) and carbon dioxide ($CO_2$) found in the patient's respiratory gases to a data processor 30. The data processor 30 receives directions for analyzing the concentrations of oxygen ($O_2$), nitrogen ($N_2$) and carbon dioxide ($CO_2$) found in the patient's respiratory gases according to a specific procedure from a program source 40. The data processor 30 outputs the results of its analysis to an alarm 50 and a display 60.

The respiratory gas analyzer 20 may be any of a variety of gas analyzers routinely used for respiratory gas analysis including a Raman gas analysis system (e.g. a Rascal® II Raman Spectrometer available through Ohmeda Inc., Louisville, Colo.) or a mass spectrometry (e.g. an MGA 1100 mass spectrometer available through Marquette Medical Gas Analyzer Co., St. Louis, Mo.). It is preferred for the present invention that a Raman gas analysis system be used since it is less expensive than a mass spectrometer, can more easily be dedicated to a single patient, and has faster response times. Detailed descriptions of Raman gas analysis systems and subsystems are presented in the following U.S. patents, each of which is hereby incorporated herein by reference: 1) U.S. Pat. No. 4,784,486, entitled "MULTI-CHANNEL MOLECULAR GAS ANALYSIS BY LASER-ACTIVATED RAMAN LIGHT SCATTERING", issued to Van Wagenen et al.; 2) U.S. Pat. No. 4,676,639, entitled "GAS CELL FOR RAMAN SCATTERING ANALYSIS BY LASER MEANS", issued to Van Wagenen; 3) U.S. Pat. No. 5,135,304, entitled "GAS ANALYSIS SYSTEM HAVING BUFFER GAS INPUTS TO PROTECT ASSOCIATED OPTICAL ELEMENTS", issued to Miles et al.; 4) U.S. Pat. Re. No. 34,153, entitled "MOLECULAR GAS ANALYSIS BY RAMAN SCATTERING IN INTRACAVITY LASER CONFIGURATION", issued to Benner et al.; and 5) U.S. Pat. No. 5,245,405 entitled "CONSTANT PRESSURE GAS CELL", issued to Mitchell et al.

In one embodiment of the venous air embolism (VAE) detector of the present invention, the detector determines if a VAE is present by analyzing the values of five breath-by-breath gas concentrations extracted from complete breath cycles (one inspiration plus one expiration). These concentrations are: 1) the maximum expired or end-tidal value for carbon dioxide ($EtCO_2$); 2) the average inspired value for nitrogen ($FiN_2$); 3) the average expired value for nitrogen ($FeN_2$); 4) the average inspired value for oxygen ($FiO_2$); and 5) the average expired value for oxygen ($FeO_2$).

Figure 2:
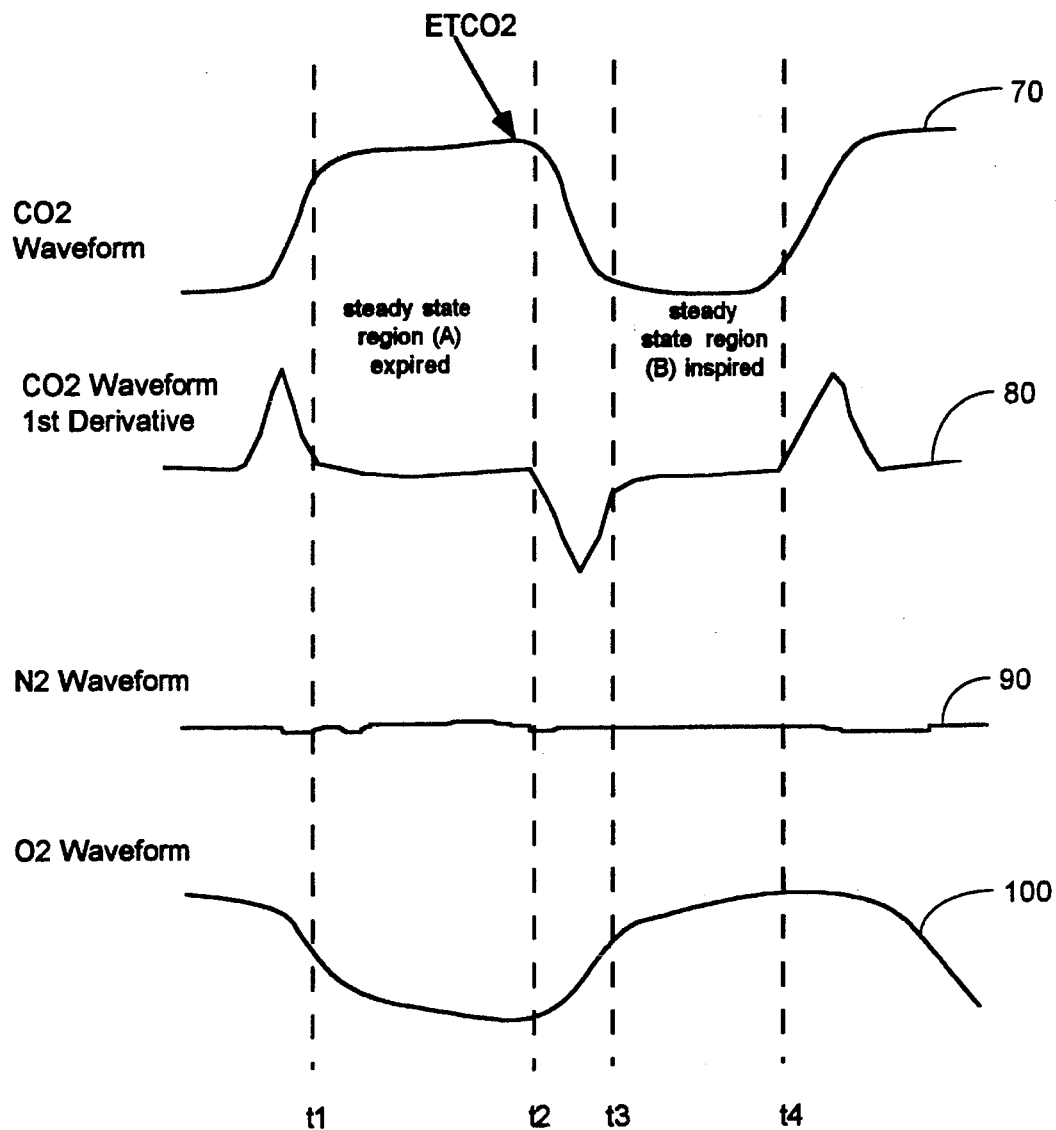
FIG. 2 is a graphical representation of a typical respiratory gas waveform.

The manner in which these gas concentration parameters are determined is described by reference to FIG. 2 which is a graphical representation of a typical respiratory gas waveform through a complete breath cycle comprising an expired portion and an inspired portion. A typical $CO_2$ waveform 70 is shown for a complete breath cycle along with the first derivative of the $CO_2$ waveform 80. Also shown is a typical $N_2$ waveform 90 and a typical $O_2$ waveform 100. The $CO_2$ waveform 70 is sampled, using a sample and hold procedure, to determine the maximum $CO_2$ concentration for each expired breath, which is defined to be the end-tidal carbon dioxide value, i.e., $EtCO_2$. The $CO_2$ waveform 70 is further analyzed by taking its first derivative 80 and applying a threshold criteria (less than 1% $CO_2$/100 msec) to define "steady state" portions of each portion of the complete breath waveform. An expired region A is defined to be the steady state region starting at time $t_1$ and ending at time $t_2$. Likewise, an inspired region B is defined to be the steady state region starting at time $t_3$ and ending at time $t_4$. The times $t_1$, $t_2$, $t_3$ and $t_4$ are determined by reference to the first derivative of the $CO_2$ waveform 80 as shown. The expired region is defined as the steady state region which corresponds to the portion of the $CO_2$ waveform 70 which exhibits the higher concentration of $CO_2$ while the inspired region is defined as the steady state region which corresponds to the portion of the $CO_2$ waveform 70 which exhibits the lower concentration of $CO_2$.

The average expired value for nitrogen ($FeN_2$) and the average inspired value for nitrogen ($FiN_2$) are determined from the $N_2$ waveform 90. The value of $FeN_2$ is defined as the average nitrogen concentration during the expired region A of the breath cycle and the value of $FiN_2$ is defined as the average nitrogen concentration during the inspired region B of the breath cycle. Similarly, the average expired value for oxygen ($FeO_2$) and the average inspired value for oxygen ($FiO_2$) are determined from the $O_2$ waveform 100. The value of $FeO_2$ is defined as the average oxygen concentration during the expired region A of the breath cycle and the value of $FiO_2$ is defined as the average oxygen concentration during the inspired region B of the breath cycle.

It is to be understood that the above described method for determining the values of the parameters $EtCO_2$, $FeN_2$, $FiN_2$, $FeO_2$ and $FiO_2$ is but one technique which may be used. Other methods may also be used to practice the present invention.

Figure 3:
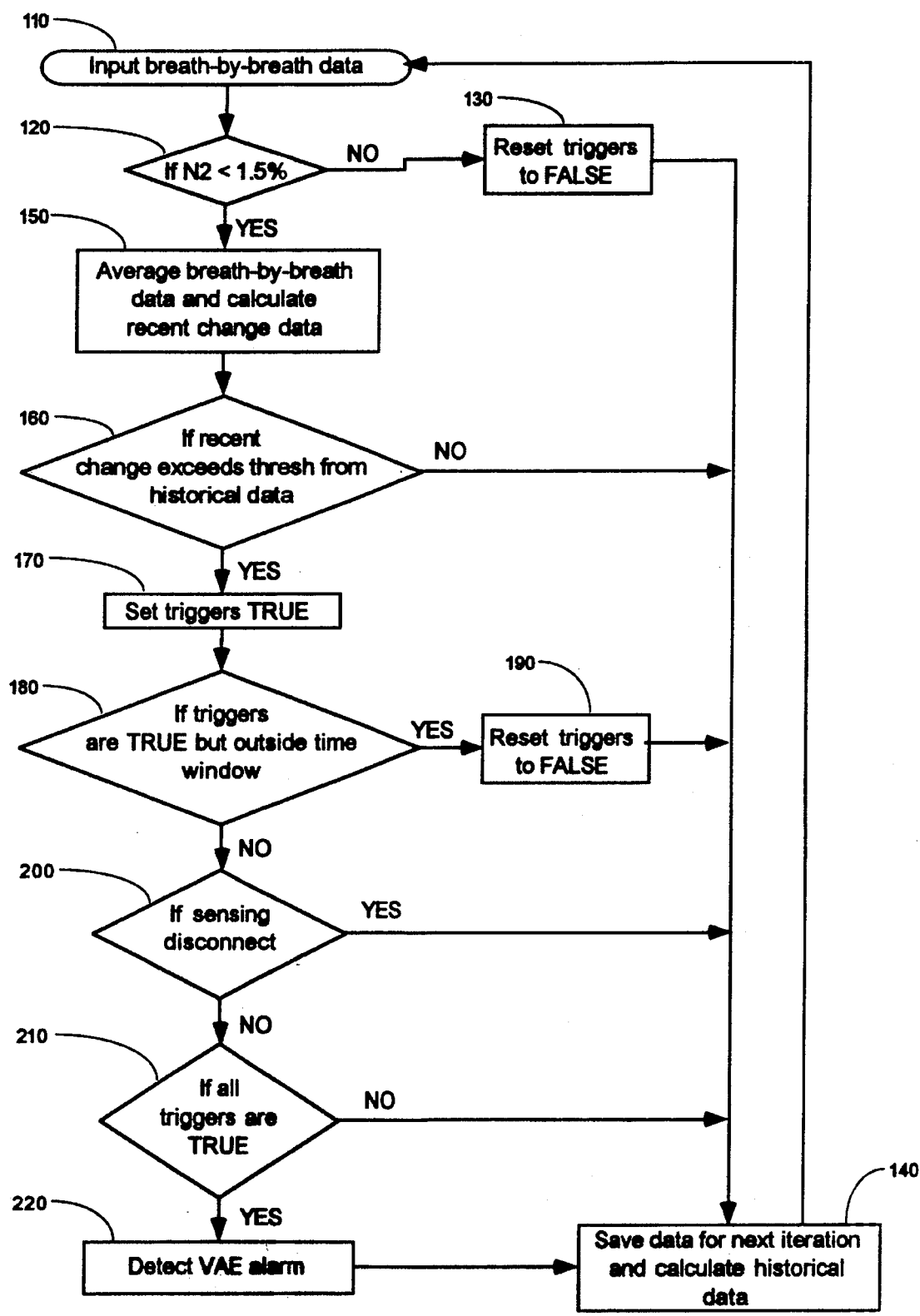
FIG. 3 shows a flow chart of the operation of the venous air embolism detection procedure.

A flow chart of the operation of the venous air embolism detection procedure represented by program source 40 (FIG. 1) is presented in FIG. 3. The process starts at an input block 110 wherein the breath-by-breath gas concentration data, i.e., the values of the parameters $EtCO_2$, $FeN_2$, $FiN_2$, $FeO_2$ and $FiO_2$, are input into the data processor 30. Input block 110 proceeds to a decision block 120 where $FeN_2$ is compared to a predetermined value, in this case 1.5%. If $FeN_2$ is greater than 1.5%, the process proceeds along the NO path to activity block 130 where the alarm triggers are set to FALSE. The process then proceeds to activity block 140 where all of the input data are saved for the next call and the process returns to the input block 110. This branch and termination of the process is necessary because the background nitrogen concentration is too high and the associated noise on the signal will overwhelm the much lower level $FeN_2$ signal arising from a VAE event.

In decision block 120, if $FeN_2$ is less than or equal to 1.5%, the process proceeds along the YES path to activity block 150 where two types of averages, a long term historical average and a recent change average are calculated. Long term historical averages and short term recent change averages are calculated for each of the following parameters: 1) the difference between the $FiO_2$ and the $FeO_2$ parameters, i.e., $FiO_2$ minus $FeO_2$, also referred to as the Delta $O_2$ value; 2) the $EtCO_2$ parameter; and 3) the $FeN_2$ parameter. One method for determining the historical averages is illustrated in FIG. 4.

Figure 4:
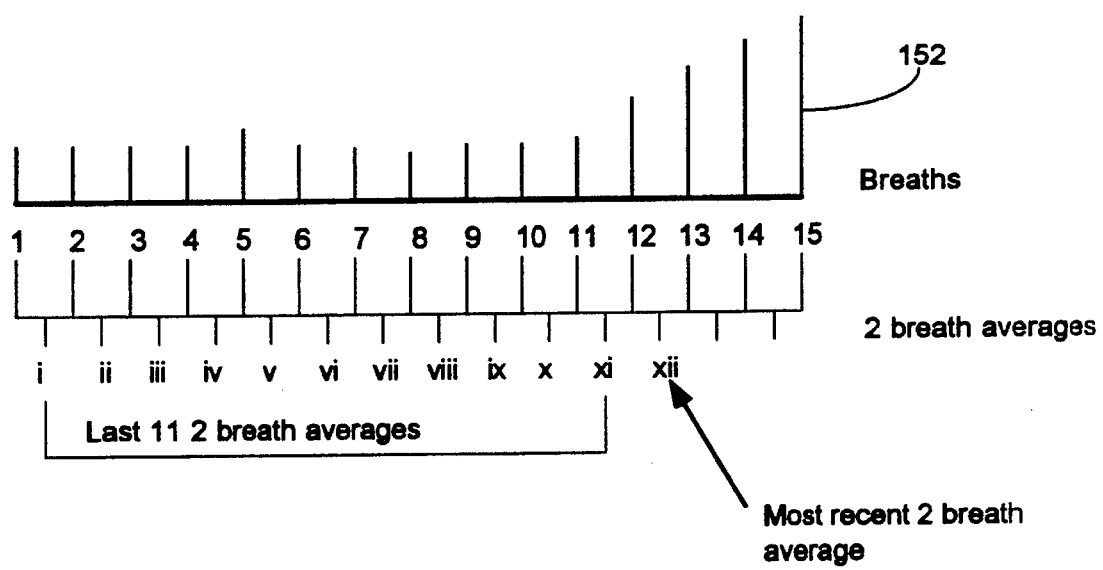
FIG. 4 is a graphical representation of a breath averaging procedure used in the present invention.

In FIG. 4, the data for 15 breaths are shown schematically as 152. The length of each bar represents the value of a particular parameter, i.e. Delta $O_2$, $EtCO_2$ or $FeN_2$, for each of 15 breaths. For the $EtCO_2$ and $FeN_2$ parameters, the corresponding long term historical average is an 11 element data base which includes the 11 most recent 2 breath averages. For example, at breath 12, the long term historical average data base for the $EtCO_2$ parameter includes as its first entry the average of the $EtCO_2$ parameter at breaths 1 and 2, i.e. i; its second entry is the average of breaths 2 and 3, i.e. ii; its third entry is the average of breaths 3 and 4, i.e. iii; . . . ; its tenth entry is the average of breaths 10 and 11, i.e. x; and its eleventh entry is the average of breaths 11 and 12, i.e. xi. At breath 13, the long term historical average data base is updated by dropping the oldest 2 breath average, i.e. entry i, and adding the most recent 2 breath average, i.e. the average of breaths 12 and 13, xii. In this manner, the historical data base for each parameter is constantly updated to always include the eleven most recent 2 breath averages.

For the Delta $O_2$ parameter, the corresponding long term historical average is an 11 element data base which includes the 11 most recent 4 breath averages. The procedure for creating and updating the Delta $O_2$ historical average data base is the same as that previously described for $EtCO_2$ and $FeN_2$ except that the averages are for 4 breaths instead of 2.

In conjunction with updating the historical data bases for the Delta $O_2$, $EtCO_2$ and $FeN_2$ parameters in activity block 150 (FIG. 3), the recent change data for each parameter is calculated. The recent change data for $EtCO_2$ is its most recent 2 breath average. Likewise, the most recent change data $FeN_2$ is its most recent 2 breath average. However, the recent change data for Delta $O_2$ is its most recent 4 breath average. After the historical average data bases and the recent change data are calculated in activity block 150, the process proceeds to a decision block 160.

In decision block 160, the most recent change data for each parameter is compared with its respective historical averages data base. Each of the following three conditions must be TRUE in order to proceed along the YES path from decision block 160 to activity block 170. First, the most recent change data for the $FeN_2$ parameter must be higher by at least 0.03 vol % than the highest of the 11 entries in the $FeN_2$ historical averages data base. (In some cases the threshold value is 0.25 vol %.) Second, the most recent change data for the $EtCO_2$ parameter must be lower by at least 1.5 mm Hg than the lowest of the 11 entries in the $EtCO_2$ historical averages data base. Third, the most recent change data for the Delta $O_2$ parameter must be lower by at least 0.2 vol % than the highest of the 11 entries in the Delta $O_2$ historical averages data base. These threshold criteria are summarized in Table I. If any one these conditions is FALSE, the process proceeds along the NO path to activity block 140 where all of the input data are saved for the next call and the process returns to the input block 110.

TABLE I

VAE Detection Threshold Criteria

| Parameter | Direction of Change | Required Change* |
|---|---|---|
| $EtCO_2$ | Down | 1.5 mm Hg |
| $FeN_2$ | Up | 0.03 vol % |
| $FiO_2 - FeO_2$ | Down | 0.20 vol % |

*Detection window = 66 seconds

If all three threshold criteria in decision block 160 are TRUE, then the process proceeds to activity block 170 where an $EtCO_2$ trigger is set to TRUE, an $FeN_2$ trigger is set to TRUE, and a Delta $O_2$ trigger is set to TRUE. The process then proceeds to decision block 180 where the timing of the three TRUE signals is tested. It is noted that the $EtCO_2$ trigger, the $FeN_2$ trigger and the Delta $O_2$ trigger must all be TRUE during the same time period, i.e., for the same breaths, to signal the presence of a VAE. For example, the current data for breaths 14 and 15 ($EtCO_2$ and $FeN_2$) and breaths 12, 13, 14 and 15 (Delta $O_2$) must all meet the three criteria shown in TABLE I. In decision block 180, the relative timing of the $EtCO_2$ trigger, the $FeN_2$ trigger and the Delta $O_2$ trigger is checked to ensure that all three TRUE triggers occurred within the same predetermined time window. If any one of the TRUE triggers occurred outside of the time window, the process proceeds along the YES path to activity block 190 where all of the triggers are reset to FALSE. The process then continues on to activity block 140 where all of the input data are saved for the next call and the process returns to the input block 110.

If the relative timing of the $EtCO_2$ trigger, the $FeN_2$ trigger and the Delta $O_2$ trigger do all occur within the same predetermined time window, the process proceeds from decision block 180 along the NO path to decision block 200. In decision block 200, a disconnect check is performed to determine if there is a disconnection in the airway circuit which would permit air to enter the system. A disconnect is signalled if: 1) the difference between the last $FiN_2$ value and the current $FiN_2$ value is greater than 25% of the current $FiN_2$; OR 2) the value of $FiN_2$ has increased by 2 vol % or more. If either of these conditions is TRUE, a disconnect alarm is activated and the process proceeds along the YES path to activity block 140 where all of the input data are saved for the next call and the process returns to the input block 110.

If neither of the two disconnect criteria are TRUE, then the process continues along the NO path to decision block 210.

If the $EtCO_2$ trigger, the $FeN_2$ trigger and the Delta $O_2$ trigger are all TRUE in decision block 210, the process proceeds along the YES path to activity block 220 where a VAE alarm is activated to signal the presence of a VAE. If any one of the $EtCO_2$ trigger, the $FeN_2$ trigger or the Delta $O_2$ trigger is FALSE in decision block 210, the process proceeds along the NO path to activity block 140 where all of the input data are saved for the next call and the process returns to the input block 110.

While the description of the VAE detector was described using the 11 breath averaging procedure illustrated in FIG. 4, other averaging scenarios are also possible. For example, the historical averages data base may be more or less than the 11 breaths illustrated and the current data may be more than the 2 breath average illustrated.

The above described VAE detection system was tested using a Raman gas analyzer in a study on dogs. In this test, the respiration rate of the dogs provided a breath output approximately every 6 seconds, thus the 11 breaths covered a 66 second time window. The results of this test are summarized in TABLE II.

TABLE II

Dog Study Test Results

| | | | <- - - RESULTS - - -> | | |
|---|---|---|---|---|---|
| Type VAE | Size VAE | # VAEs | True Pos | False Neg | False Pos |
| 1. Arterial Bolus | 2.0 ml/kg | 5 | 5 | 0 | 1 |
| 2. Venous Infusion | 2.0 ml/kg** | 4 | 4 | 0 | 1 |
| 3. Venous Bolus | 2.0 ml/kg | 6 | 6 | 0 | 1 |
| 4. Graded V. Bolus | 0.2 ml/kg | 4 | 4 | 0 | 0 |
| OVERALL TOTAL | | 19 | 19 | 0 | 3 |
| Opportunities | | 19 | 19 | 19 | 22 |
| Percent | | 100% | 100% | 0% | 14% |

Ratio: False Positives to True Positives = 0.16
**0.1 ml/kg/min for 20 minutes

It will be understood that the apparatus and method of the present invention for a venous air embolism detector may be employed with many different types of respiratory gas analysis systems including Raman and mass spectrometer. Additionally, the selection of a specific averaging technique and specific threshold criteria may vary. Thus, there are numerous other embodiments of the venous air embolism detector which will be obvious to one skilled in the art, including but not limited to changes in the specific averaging technique and threshold criteria, the type of gas analysis system used, the number of gas parameters used, the comparison technique used, for instance comparison of the most recent breath to a running average to establish baseline instead of the highest or lowest value, etc. The apparatus and method of the present invention may be embodied in other specific forms without departing from its spirit or essential characteristics. The described embodiments are to be considered in all respects only as illustrative and not restrictive.

The scope of the invention is, therefore, indicated by the appended claims rather than by the foregoing description. All changes which come within the meaning and range of equivalency of the claims are to be embraced within their scope.

We claim:

1. An apparatus for detecting an air embolism comprising:
   a respiratory gas nitrogen detector for detecting nitrogen in respiratory gases, said respiratory gas nitrogen detector having a signal output port which provides a nitrogen concentration signal representative of a concentration of the nitrogen detected in the respiratory gases; and
   a processor having a signal input port connected to said respiratory gas nitrogen detector signal output port, said processor further comprising:
      an historical data base of previously acquired nitrogen concentration signals;
      a threshold analyzer having an input which receives the previously acquired nitrogen concentration signals from said historical data base and an output which provides a nitrogen concentration baseline threshold value according to a predetermined analysis criteria;
      a current data register which receives and stores a current nitrogen concentration signal from said respiratory gas nitrogen detector; and
      a comparator which compares the current nitrogen concentration signal with the nitrogen concentration baseline threshold value derived from said historical data base and triggers a venous air embolism alarm signal if the current nitrogen concentration signal crosses within a predetermined time window.

2. An apparatus as defined in claim 1 wherein said respiratory gas nitrogen detector is a Raman gas analyzer.

3. An apparatus as defined in claim 1 wherein:
   said threshold analyzer further comprises a peak detector which searches said historical data base of previously acquired nitrogen concentration signals; determines a maximum historical nitrogen concentration value therein; and sets the nitrogen concentration baseline threshold value equal to the maximum historical nitrogen concentration value; and
   said comparator further comprises a difference unit which determines a difference between the maximum historical nitrogen concentration value and the current nitrogen concentration signal held in the current data register and triggers the venous air embolism alarm signal if the difference exceeds a predetermined difference criteria.

4. An apparatus as defined in claim 1 wherein said historical data base of previously acquired nitrogen concentration signals and the current nitrogen concentration signal are end-tidal nitrogen concentrations, $FeN_2$.

5. An apparatus as defined in claim 1 wherein said threshold analyzer further comprises an averager which determines an average historical value derived from the historical data base of previously acquired nitrogen concentration signals and gets the nitrogen concentration baseline threshold value equal to the average historical value.

6. An apparatus for detecting an air embolism comprising:
   a respiratory gas detector which detects carbon dioxide and nitrogen in respiratory gases, said respiratory gas detector having a signal output port which provides a carbon dioxide concentration signal and a nitrogen concentration signal which are representative of a concentration of carbon dioxide and a concentration of nitrogen, respectively, in the respiratory gases; and
   a comparator having a signal input port connected to said respiratory gas detector signal output port wherein said comparator compares said carbon dioxide and nitrogen concentration signals with a predetermined carbon dioxide concentration threshold and a predetermined nitrogen concentration threshold, respectively, said comparator having an output which triggers an air embolism alarm when said carbon dioxide and nitrogen concentrations both cross said predetermined carbon dioxide concentration threshold and said predetermined nitrogen concentration threshold, respectively, within a predetermined time window.

7. An apparatus as defined in claim 6 wherein said respiratory gas detector is a Raman gas analyzer.

8. An apparatus as defined in claim 6 wherein:
   said respiratory gas detector further comprises means for detecting oxygen in the respiratory gases, said means for detecting oxygen having a signal output port which provides an oxygen concentration signal which is representative of a concentration of oxygen in the respiratory gases; and
   said comparator further comprises a predetermined oxygen concentration threshold and triggers said air embolism alarm when said carbon dioxide, nitrogen and oxygen concentration signals cross said predetermined carbon dioxide concentration threshold, said predetermined nitrogen concentration threshold and said predetermined oxygen concentration threshold, respectively, within said predetermined time window.

9. An apparatus for detecting an air embolism comprising:
   a detector means for detecting nitrogen and carbon dioxide in respiratory gases;
   a gas analyzer means for determining a plurality of breath-by-breath inspired and expired concentrations of the nitrogen and carbon dioxide detected by said detector means in the respiratory gases;
   an end-tidal carbon dioxide analyzer means which receives the plurality of breath-by-breath inspired and expired concentrations of the carbon dioxide from said gas analyzer means and determines a plurality of breath-by-breath end-tidal carbon dioxide concentration values, $EtCO_2$, therefrom for a plurality of breaths;
   an end-tidal carbon dioxide data memory means for storing the plurality of breath-by-breath end-tidal carbon dioxide concentration values, $EtCO_2$, received from said end-tidal carbon dioxide analyzer means as a function of time;
   a nitrogen analyzer means which receives the plurality of breath-by-breath inspired and expired concentrations of the nitrogen from said gas analyzer means and determines a plurality of breath-by-breath expired nitrogen concentration values, $FeN_2$, therefrom for a plurality of breaths;
   an expired nitrogen data memory means for storing the plurality of breath-by-breath expired nitrogen concentration values, $FeN_2$, received from said nitrogen analyzer means as a function of time; and
   a processor means which 1) compares a current breath value of $EtCO_2$ for a current breath with the plurality of breath-by-breath end-tidal carbon dioxide concentration values, $EtCO_2$, stored in said end-tidal carbon dioxide data memory means and sets an $EtCO_2$ TRUE flag for the current breath is a predetermined $EtCO_2$ comparison criteria is satisfied; 2) compares a corresponding current breath value of $FeN_2$ for the current breath with the plurality of breath-by-breath expired nitrogen concentration values, $FeN_2$, stored in said expired nitrogen data memory means and sets an $FeN_2$ TRUE flag for the current breath if a predetermined $FeN_2$ comparison criteria is satisfied; and 3) signals an alarm if the $EtCO_2$ TRUE flag for the current breath and the $FeN_2$ TRUE flag for the current breath are both set.

10. An apparatus as defined in claim 9 further comprising:

said detector means which further comprises an oxygen detector means which detects oxygen in the respiratory gases;

said gas analyzer means which further comprises an oxygen analyzer means which determines a plurality of breath-by-breath inspired and expired concentrations of the oxygen detected by said oxygen detector means in the respiratory gases;

an oxygen analyzer means which receives the plurality of breath-by-breath inspired and expired concentrations of the oxygen from said oxygen analyzer means and determines a plurality of breath-by-breath inspired oxygen minus expired oxygen concentration values, $FiO_2$–$FeO_2$, therefrom for a plurality of breaths;

an oxygen data memory means for storing the plurality of breath-by-breath inspired oxygen minus expired oxygen concentration values, $FiO_2$–$FeO_2$, received from said oxygen analyzer means as a function of time; and said processor means further comprises means which 4) compares a current breath value of $FiO_2$–$FeO_2$ for the current breath with the plurality of breath-by-breath inspired oxygen minus expired oxygen concentration values, $FiO_2$–$FeO_2$, stored in said oxygen data memory means and sets an $FiO_2$–$FeO_2$ comparison criteria is satisfied; and 5) signals an alarm if the $EtCO_2$ TRUE flag for the current breath, the $FeN_2$ TRUE flag for the current breath and the $FiO_2$–$FeO_2$ TRUE flag for the current breath are all set.

11. An apparatus as defined in claim 9 wherein said detector means is a Raman gas analyzer.

12. An apparatus as defined in claim 9 further comprising:

a maximum value detector means which extracts a maximum $FeN_2$ value from the plurality of breath-by-breath expired nitrogen concentration values, $FeN_2$, as a function of time which are stored in the expired nitrogen data memory means; and a comparator means which compares the corresponding current breath value of $FeN_2$ with the maximum $FeN_2$ value and triggers an alarm when the corresponding current breath value of $FeN_2$ exceeds the maximum $FeN_2$ value by at least 0.01 vol %.

13. An apparatus as defined in claim 9 further comprising:

a minimum value detector means which extracts a minimum $EtCO_2$ value from the plurality of breath-by-breath end-tidal carbon dioxide concentration values, $EtCO_2$, as a function of time which are stored in the end-tidal carbon dioxide data memory means; and a comparator means which compares the current breath value of $EtCO_2$ with the minimum $EtCO_2$ value and triggers an alarm when the current breath value of $EtCO_2$ is lower the minimum $EtCO_2$ value by at least 1.0 mmHg.

14. A method of automatically detecting an air embolism comprising:

detecting nitrogen in respiratory gases;

determining, from the nitrogen detected in the respiratory gases, a plurality of breath-by-breath expired nitrogen concentrations for a plurality of breaths and storing the plurality of breath-by-breath expired nitrogen concentrations in a nitrogen historical data base;

comparing a recent expired nitrogen concentration value of the plurality of breath-by-breath expired nitrogen concentrations with the plurality of breath-by-breath expired nitrogen concentrations stored in the nitrogen historical data base; and signalling an air embolism event when the recent expired nitrogen concentration value of the plurality of breath-by-breath expired nitrogen concentrations crosses a nitrogen baseline threshold derived from the nitrogen historical data base of breath-by-breath expired nitrogen concentrations.

15. A method as defined in claim 14 further comprising:

detecting carbon dioxide in respiratory gases;

determining, from the carbon dioxide detected in the respiratory gases, a plurality of breath-by-breath end-tidal carbon dioxide concentrations for a plurality of breaths and storing the plurality of breath-by-breath end-tidal carbon dioxide concentrations in a carbon dioxide historical data base;

comparing a recent end-tidal carbon dioxide concentration value of the plurality of breath-by-breath end-tidal carbon dioxide concentrations with the plurality of breath-by-breath end-tidal carbon dioxide concentrations stored in the carbon dioxide historical data base; and signalling the air embolism event when the recent end-tidal carbon dioxide concentration value of the plurality of breath-by-breath end-tidal carbon dioxide concentrations crosses a carbon dioxide baseline threshold derived from the carbon dioxide historical data base of breath-by-breath end-tidal carbon dioxide concentrations and the recent expired nitrogen concentration value of the plurality of breath-by-breath expired nitrogen concentrations crosses the nitrogen baseline threshold derived from the nitrogen historical data base of breath-by-breath expired nitrogen concentrations.

16. A method as defined in claim 15 wherein signalling the air embolism event further comprises:

defining the nitrogen baseline threshold to be a maximum expired nitrogen concentration in the nitrogen historical data base; and setting a nitrogen trigger when the recent expired nitrogen concentration value of the plurality of breath-by-breath expired nitrogen concentrations exceeds the nitrogen baseline threshold by at least 0.01 vol %.

17. A method as defined in claim 15 wherein signalling the air embolism event further comprises:

defining the carbon dioxide baseline threshold to be a minimum end-tidal carbon dioxide concentration in the carbon dioxide historical data base; and setting an end-tidal carbon dioxide trigger when the recent end-tidal carbon dioxide concentration value of the plurality of breath-by-breath end-tidal carbon dioxide concentrations is lower than the carbon dioxide baseline threshold by at least 1.0 mmHg.

18. A method as defined in claim 14 wherein signalling an air embolism event further comprises:

defining the nitrogen baseline threshold to be a maximum expired nitrogen concentration in the nitrogen historical data base; and triggering a nitrogen error alarm when the recent expired nitrogen concentration value of the plurality of breath-by-breath expired nitrogen concentrations exceeds the nitrogen baseline threshold by at least 0.01 vol %.

* * * * *

UNITED STATES PATENT AND TRADEMARK OFFICE
CERTIFICATE OF CORRECTION

PATENT NO. : 5,533,512
DATED : July 9, 1996
INVENTOR(S) : Mark Alan Novotny, Thomas Arthur Boone, Jeffrey D. Geisler, Garfield Barry Russell and John Milton Graybeal It is certified that error appears in the above-identified patent and that said Letters Patent is hereby corrected as shown below:

In column 11, at line 31, that portion reading "crosses within" should read --crosses the nitrogen concentration baseline threshold value within--;

In column 11, at line 56, that portion reading "gets" should read --sets--;

In column 12, at line 59, that portion reading "breath is" should read --breath if--;

In column 13, at line 27, that portion reading "an $FiO_2$-$FeO_2$ comparison" should read --an $FiO_2$-$FeO_2$ TRUE flag for the current breath if a predetermined $FiO_2$-$FeO_2$ comparison--;

In column 14, at line 35, that portion reading "claim 15" should read --claim 14--;

UNITED STATES PATENT AND TRADEMARK OFFICE
CERTIFICATE OF CORRECTION

PATENT NO.   :   5,533,512
DATED        :   July 9, 1996
INVENTOR(S)  :   Mark Alan Novotny, Thomas Arthur Boone, Jeffrey D. Geisler,
                 Garfield Barry Russell and John Milton Graybeal It is certified that error appears in the above-identified patent and that said Letters Patent is hereby corrected as shown below:

```
     In column 14, at line 36, that portion reading "the air"
should read --an air--;
     In column 14, at line 40, that portion reading "setting a
nitrogen trigger when" should read --triggering a nitrogen error
alarm when--;
     In column 14, at line 54, that portion reading "claim 14"
should read --claim 15--;
     In column 14, at line 54, that portion reading "signalling
an" should read --signalling the--; and
     In column 14, at line 59, that portion reading "triggering
a nitrogen error alarm when" should read --setting a nitrogen
trigger when--.
```

Signed and Sealed this

Seventeenth Day of February, 1998

*Attest:*

BRUCE LEHMAN

*Attesting Officer*    Commissioner of Patents and Trademarks